United States Patent [19]

Morimoto et al.

[11] Patent Number: 4,543,330

[45] Date of Patent: Sep. 24, 1985

[54] PROCESS FOR THE PRODUCTION OF A FERMENTATION STARTING MATERIAL

[75] Inventors: Hideyuki Morimoto, Yokohama; Masaru Saeki, Fujisawa; Tetsuya Kawakita, Yokohama, all of Japan

[73] Assignee: Ajinomoto Co., Inc., Tokyo, Japan

[21] Appl. No.: 567,673

[22] Filed: Jan. 3, 1984

[30] Foreign Application Priority Data

Nov. 10, 1982 [JP]  Japan ................................ 57-197139
Nov. 10, 1982 [JP]  Japan ................................ 57-197138

[51] Int. Cl.$^4$ ............................................. C12P 13/14
[52] U.S. Cl. ................................... 435/110; 127/46.3
[58] Field of Search .................... 127/36, 41, 46.3, 56; 435/99, 105, 110

[56] References Cited

U.S. PATENT DOCUMENTS 4,066,502  1/1978  Asai et al. ........................ 435/110
4,332,622  6/1982  Hohnerlein et al. ................ 127/41

*Primary Examiner*—Ivars Cintins
*Attorney, Agent, or Firm*—Oblon, Fisher, Spivak, McClelland & Maier

[57] ABSTRACT

A process for the production of a fermentation starting material from cane molasses which comprises: inverting most of the sugar contained in cane molasses either enzymatically with invertase or with a mineral acid, passing the cane molasses containing invert sugar through a column containing a cation exchange resin, eluting invert sugar from the resin with water (pH 5–8), and obtaining an eluate fraction containing the invert sugar to be used as a carbon source for the production of L-glutamic acid by a fermentation technique.

11 Claims, No Drawings

PROCESS FOR THE PRODUCTION OF A FERMENTATION STARTING MATERIAL

DETAILED DESCRIPTION OF THE INVENTION

This invention relates to a process for the production of a fermentation starting material from cane molasses, and more specifically, it relates to a method for modifying cane molasses so it is more suitable as a carbon source when producing L-glutamic acid by a fermentation technique.

Cane molasses is a by-product containing sucrose which is produced in the sugar-manufacturing industry, and is employed as a preferred carbon source when producing L-glutamic acid by a fermentation technique.

The present inventors have been studying in order to improve such cane molasses for use as a more preferred starting material for producing L-glutamic acid, and have discovered that by passing cane molasses through a resin column packed with a cation form cation exchange resin, passing water having a pH in the range of 5-8 through the resin column, obtaining an eluate fraction containing sugar eluted therewith and producing L-glutamic acid by a fermentation using this fraction as a carbon source, L-glutamic acid can be produced in a higher yield as compared with a case where the original cane molasses is employed as a carbon source.

Based on the above discovery, the present inventors have furthered the research for the modification of cane molasses and have come to discover that further by preliminarily inverting sucrose by adding an invertase or a mineral acid in the cane molasses before the aforesaid chromatography step using an ion exchange resin, the recovery of the sugar in the chromatography step is enhanced.

Accordingly, there has now been presented the following invention.

That is, this invention is a process for the production of a fermentation starting material which comprises a step (1) of adding an invertase or a mineral aeid to cane molasses and keeping said cane molasses to which the invertase or the mineral acid has been added at a temperature and a pH suitable for inversion for a time required for almost all the amount of the sugar contained in said cane molasses to be inverted (inversion step), a step (2) of passing said cane molasses treated with the invertase or the mineral acid after the step (1) through a column packed with a cation form cation exchange resin and subsequently passing water having a pH in the range of 5-8 in an amount enough to elute 97% or more of the invert sugar through said resin column (chromatography step), and a step (3) of obtaining an eluate fraction containing the invert sugar after the step (2) as a carbon source for the production of L-glutamic acid by a fermentation.

In the above-described process for the production of a fermentation starting material, if a step (4) of passing the cane molasses through a column packed with a potassium form cation exchange resin (ion exchange step) is conducted between the step (1) and the step (2) and also if a potassium ion form cation exchange resin is employed as the cation form cation exchange resin in the step (2), the recovery efficiency of the sugar is higher and also the productivity of L-glutamic acid is higher.

Heretofore, it has been known that by inverting sugar contained in cane molasses using an invertase and producing L-glutamic acid by a fermentation using the thus obtained invert sugar, the productivity of L-glutamic acid is higher than a case where non-invert sugar is employed (Japanese patent application Laid-open No. 85290/1981), but it is a new discovery that by preliminarily inverting sugar in cane molasses using an invertase or a mineral acid, the refining efficiency of sugar in cane molasses by chromatography using a cation form cation exchange resin is even higher, and further although it is known that sugar in cane molasses is refined by chromatography using a strongly acidic cation exchange resin (for example, K. Sayama et al., Chromatographic Separation of Molasses Constituents, Part 1, Recovery of Sucrose from Molasses, "Journal of Sugar Refining Technique Research Association", No. 29, 1-9 (1980)), it is not known that by using the sugar thus refined, the productivity of L-glutamic acid is enhanced. Further, it is known that an acid hydrolysate of molasses may be subjected to chromatography using a sulfurous acid form or hydrogen sulfite form ion exchange resin to obtain refined glucose and fructose (Japanese Patent Publication No. 28680/1980), but even when L-glutamic acid produced by a fermentation technique by employing such glucose and fructose refined by this method, L-glutamic acid is not produced at as high efficiency as when L-glutamic acid is produced employing invert sugar refined with a cation exchange resin.

As the invertase, commercially available enzymes and also yeast microbial cells having invertase activity and their treated products can be employed.

As the yeast, yeast belonging to the genus Saccharomyces, the genus Candida, the genus Mycotorula, the genus Debaryomyces, the genus Pichia, the genus Hansenula and the genus Torulopsis are employed and further, the yeast microbial cells obtained by culturing these yeasts in media containing molasses, glucose, pulp production waste liquor, soybean whey, food industry waste liquor, juice etc. are employed. As the yeast microbial cell treated products, there are employed dried microbial cells obtained by merely drying the microbial cells (baker's yeast, brewing waste liquor yeast etc.), residues after removing useful ingredients such as yeast extract, RNA, glutathione etc. from yeast microbial cells, autodigested microbial cell residues, physically smashed microbial cells, microbial cells treated with lysozyme, toluene, surfactant etc., and the like.

In order to invert sucrose in molasses using an invertase, the molasses is diluted to an appropriate concentration, for example, 10-50 g/dl, the aforesaid invertase source is added thereto, and an enzymatic reaction is effected by maintaining 20°-60° C. for 5-20 hours.

The inversion of the sucrose with an acid is effected in the conventional manner of adjusting the pH of the molasses to 1.0-4.0 by adding hydrochloric acid or sulfuric acid and heating to a temperature of 80°-110° C. After the acid hydrolysis, the system is neutralized by adding an alkali such as sodium hydroxide. Where precipitates are formed during the acid decomposition to neutralization steps, it is desirable to remove the precipitates and thus the purification effect is further enhanced.

The cation exchange resin used in this invention is preferably a stongly acidic cation exchange resin such as Amberlite IR-120, Dowex-50, Diaion SK-1BS.

Such a cation exchange resin is more preferably in a sodium or potassium form. The aforesaid ion exchange resin is packed in a column of an appropriate size, then cane molasses already subjected to the inversion step is supplied to this packed column, and subsequently invert sugar is eluted with water having a pH in the range of 5-8. The eluting order is as follows: colored substances and inorganic salts are firstly eluted, and thereafter glucose and fructose are eluted in that order. After the chromatography, the fraction containing invert sugar, i.e. glucose and fructose, is collected, thereby the sugar can be separated from extraneous matters.

The column to be employed is preferably a column equipped with a heat retaining jacket and desirably the temperature within the column is maintained at 50°-90° C. The sugar concentration of invert sugar to be passed through said column is suitably in the range of 15-50 g/dl calculated as sucrose, desirably more economically 35-45 g/dl. Further, the liquid passing rate is preferably in the range of 0.5-2 S.V.

The eluate by the above described chromatography is divided into the following fractions:

First fractions: a fraction from the initial eluate up to elution of solids (extraneous matters of molasses);

Second fraction: a fraction from the end point of the first fraction until the concentration of the extraneous matters reaches about $\frac{1}{2}$-$\frac{1}{3}$ of the peak value of the measured value of electrical conductance;

Third fraction: a fraction from the end point of the second fraction until the concentration of invert sugar reaches about 1-5 g/dl;

Fourth fraction: a fraction from the end point of the third fraction until the concentration of the extraneous matters reaches about $\frac{1}{2}$-$\frac{1}{3}$ of the peak value of the measured value of electrical conductance;

Fifth fraction: a fraction from the end point of the fourth fraction until the concentration of invert sugar reaches about $\frac{1}{2}$-$\frac{1}{3}$ of the peak value;

Sixth fraction: a fraction from the end point of the fifth fraction until the concentration of invert sugar reaches about 1 g/dl.

Among these fractions, the fifth fraction is the fraction containing the invert sugar to be collected, and the third fraction is separately collected as the fraction containing extraneous matters. The second fraction is preferably supplied to the resin column of the next batch of chromatography prior to the supply of cane molasses already subjected to the inversion step. Further, the fourth and sixth fractions are preferably supplied to the resin column after supplying cane molasses of the next batch already subjected to the inversion step to the resin column. Furthermore, the first fraction is preferably reused as water having a pH of 5-8 for elution.

By repeating this operation, equilibrium is generally reached after 5 or 6 times, thereby the stable separation of the extraneous matters and invert sugar can be effected. In other words, the fraction mainly containing extraneous matters contained in molasses is recovered as the third fraction, and the fraction of invert sugar containing only very small amounts of extraneous matters is recovered as the fifth fractions.

Prior to the above-described chromatography, if the cane molasses already subjected to the inversion step is subjected to a step of passing through a column packed with a potassium ion form cation exchange resin and also if the cation form cation exchange resin in the chromatography step is a potassium ion form, then the refining efficiency of invert sugar is further enhanced. The cation exchange resin is preferably a strongly acidic cation exchange resin similarly as in the chromatography step. By this step, almost all the cations in the molasses become potassium ions.

The operating temperature in the ion exchange step is from room temperature to 90° C., preferably 50°-80° C., and the supply rate is 0.5-5 S.V. (eluted volume/resin volume×period of time). At a point where the ion exchange capacity of the ion exchange resin in exceeded and the eluted cane molasses showed incorporation of about 1-7% calculated as ion equivalent of other cations, then the supply of the molasses is stopped. The ion exchange resin can be reused repeatedly by regeneration, and said regeneration may be effected in the conventional manner using any regenerator.

Further, the burden of the ion exchange resin in the ion exchange step can be lightened by, prior to the ion exchange step, removing solids, i.e. the so-called sludge, contained in the molasses by passing cane molasses already subjected to the inversion step through an ultrahigh speed centrifugal separator, for example, Model SAOH manufatured by Westfalia , etc. or removing turbidity and at the same time calcium salts by adding phosphoric acid or a phosphoric acid salt.

In order to produce L-glutamic acid by a fermentation technique using the thus obtained sugar as a carbon source, any kind of the conventionally employed microorganisms capable of producing L-glutamic acid can be employed, and the medium and conditions for culturing a microorganism employed in this invention is nothing particular.

Examples of the conventionally known microorganisms capable of producing L-glutamic acid include:
Brevibacterium flavum ATCC 14067,
Brevibacterium lactofermentum ATCC 13869,
Brevibacterium saccharolyticum ATCC 14066,
Brevibacterium thiogentalis ATCC 19240,
Corynebacterium glutamicum ATCC 13032,
Corynebacterium melassecola ATCC 17965.

While the carbon source contained in the medium is the sugar obtained by the process of this invention, it is possible to use in combination therewith other carbon sources such as beet molasses, crude sugar, an acid or enzyme hydrolysate of starch, etc.

By conducting L-glutamic acid fermentation by employing the fermentation starting material prepared by the process of this invention, L-glutamic acid can be produced at higher efficiency than a case where cane molasses is employed. Further, such an effect to enhance the efficiency cannot be obtained even by the same steps as in the process of this invention if beet molasses is employed, and therefore, this is a phenomenon characteristic to cane molasses. Furthermore, since the recovery of sugar in cane molasses by the process of this invention is extremely high and, in addition, satisfactorily refined sugar is obtained, L-glutamic acid can be more easily obtained from L-glutamic acid fermentation broth.

EXAMPLE 1

(1) Inversion Step (a) Inversion with Invertase

To cane molasses adjusted to a sugar concentration of 55 g/dl by diluting with water was added a commercially available "Biocon" (yeast microbial cell wall dried product produced by Biocon Co.) at a rate of 1.2 mg per g of sugar, and maintained at 55° C. for 10 hours to effect an enzymatic reaction.

(b) Inversion with Acid

To cane molasses adjusted to a sugar concentration of 55 g/dl by adding water was added sulfuric acid to adjust the pH of the molasses to 1.5, and this was maintained at a temperature of 100° C. for 20 minutes to effect a decomposition reaction, after which the reaction mixture was cooled, neutralized (pH 6.0) by adding sodium hydroxide and filtered.

(2) Chromatography Step (a) Cation Exchange Resin Treatment 30 ml of molasses adjusted to a sugar concentration of 40 g/dl was supplied to a column packed with 240 ml of a K form cation exchange resin ("Diaion SK-1BS"), and eluted with water. The temperature was maintained at 70° C., and the water supplying rate was set 12 /hr. The eluate was analyzed by high speed liquid chromatography, and fractions containing glucose, fructose and sucrose were collected to recover 93% of sugar. The amount of sugar recovered, as solids, was measured and the sugar purity was calculated.

(b) Anion Exchange Resin Treatment 30 ml of molasses adjusted to a sugar concentration of 40 g/dl was supplied to a column packed with 240 ml of a sulfurous acid form anion exchange resin ("Amberlite IRA-400"), and eluted with water. The temperature was kept at 40° C., and the water supplying speed was 12 /hr. The sugar concentration of the eluate and the total solids concentration was measured, and the sugar concentration of the sugar fraction in which 93% of sugar was recovered was calculated.

(3) L-Glutamic Acid Fermentation

By the experimental constitution set forth in Table 1, cane molasses used as a starting material was successively treated by the above-described conditions, and the obtained sugar was presented to a fermentation test. That is, the obtained molasses was concentrated to a sugar concentration of 50%, and 50 ml thereof was mixed with 250 ml of a salt solution having the composition set forth in Table 1 and thus 300 ml of a medium for fermentation of glutamic acid was prepared.

TABLE 1

| Composition of Salt Solution | |
| --- | --- |
| Component | Content |
| KH$_2$PO$_4$ | 2.0 g |
| MgSO$_4$.7H$_2$O | 0.5 " |
| FeSO$_4$.7H$_2$O | 10 mg |
| MnSO$_4$.4H$_2$O | 10 " |
| Thiamine hydrochloride | 200 μg |
| Soybean protein hydrolysate (TN 4 g/dl) | 50 μg |

TABLE 1-continued

| Composition of Salt Solution | |
| --- | --- |
| Component | Content |
| Biotin* | 300 μg |

*Added in the case of a sugar solution separated by chromatography 300 ml portions of the thus prepared medium for producing L-glutamic acid were charged into 1.0 l fermentors respectively, and sterilized by heating at 115° C. for 10 minutes. Each was inoculated with previously cultured Brevibacterium lactofermentum ATCC 13869 and while the pH was maintained at 7.8 with ammonia gas at 31.5° C., culture was effected while stirring with aeration. Culture was conducted for 36 hours while adjusting the sugar concentration to between 2% and 4% by adding a small amount of each sugar solution employed when the sugar concentration calculated as sucrose in the medium dropped below 3% during culture.

The amounts of the sugar solutions added were made 80 ml in the all experimental sections. Further, at a point when a predetermined amount of cells has been reached during culture, a surfactant "Tween 60" was added so as to give 0.6% per medium.

(4) Results

The results of the experiments thus conducted are shown in Table 2. Table 2 shows the percent of impurities removed of the sugar fraction obtained when the chromatography step was conducted (percent of extraneous matters other than sugar removed), the amount of L-glutamic acid accumulated in the culture and its yield based on sugar in the fermentation test.

TABLE 2

| | Sugar Concentration and Fermentation Yield | | | | | | |
| --- | --- | --- | --- | --- | --- | --- | --- |
| | Pre-treatment | | Chromatography Treatment | | | L-Glumatic Acid | |
| Experiment No. | Invertase Treatment | Acid Treatment | Cation Exchange Resin | Anion Exchange Resin | Percent of Impurities Removed (%) | Amount Accumulated (g/dl) | Yield Based on Sugar (%) |
| 1 | — | — | — | — | — | 7.52 | 46.4 |
| 2 | o | — | — | — | — | 7.98 | 48.0 |
| 3 | — | o | — | — | — | 7.95 | 47.7 |
| 4 | — | — | o | — | 21% | 8.10 | 50.0 |
| 5 | o | — | o | — | 58% | 8.50 | 52.5 |
| 6 | — | o | o | — | 56% | 8.39 | 51.8 |
| 7 | — | — | — | o | 34% | 7.95 | 49.1 |
| 8 | o | — | — | o | 38% | 8.00 | 49.4 |
| 9 | — | o | — | o | 37% | 7.99 | 49.3 |

—: not done
o: done

EXAMPLE 2

Water was added to cane molasses to make the sugar concentration about 50 g/dl, then a commercially available "Biocon" (yeast cell wall dried product produced by Biocon Co.) was added at a rate of 1.2 mg per g of sugar as an invertase source, and the mixture was maintained at 55° C. for 10 hours to effect an enzymatic reaction. The jacket temperature of a column (30φ 300 mm) packed with 240 ml of a K form cation exchange resin (Diaion SK-1B) was maintained at 50° C. and the invertase-treated molasses was adjusted to 50° C. and supplied at an S.V. of 2 (480 ml/hr), and 500 ml of the molasses eluted from the packed column was recovered. This molasses already subjected to the ion exchange step was analyzed for Na, K, Mg, Ca and NH$_3$ by atomic absorption sepectroscopy and high speed liquid chromatography to find that 98% of the ion equivalent had been substituted by K.

A jacketed column (Pyrex column 30φ×300 mm manufactured by Kyowa Seimitsu Co.) packed with 240 ml of a K form cation exchange resin (Diaion SK 104 S) was maintained at 60° C., and 30 ml of the molasses already subjected to the invertase treatment step and the above-described ion exchange step and also maintained at 60° C. was supplied at 60° C. The eluate was fractionated into 12 ml portions, and each fraction was analyzed by high speed liquid chromatography. As a control, similar chromatography was conducted on molasses which had been subjected to invertase treatment with no ion exchange step. In any chromatography, the sugar concentration supplied was adjusted to 40 g/dl.

After the chromatography, the sugar fractions were collected, thereby 93% of sugar was recovered. The percent of impurities removed (percent of extraneous matters other than sugar removed) of this sugar solution was 71%. On the contrary, the percent of impurities removed in the control case where ion exchange treatment was not conducted was 54%, and thus it can be seen that separability is greatly enhanced by the ion exchange treatment.

Further by conducting chromatography repeatedly, sugar fractions were removed for both cases where ion exchange treatment had been conducted and where ion exchange treatment had not been conducted, and the percent of impurities removed of each sugar solution was determined. The results thereof are shown in Table 3.

TABLE 3

| | Change in Percent of Impurities Removed | | | |
|---|---|---|---|---|
| | Ion Exchange Conducted | | Ion Exchange Treatment Non-conducted | |
| No. of Chromatography | Percent of Sugar Recovered | Percent of Impurities Removed | Percent of Sugar Recovered | Percent of Impurities Removed |
| 1st | 93% | 71% | 92% | 54% |
| 5th | 95% | 73% | 93% | 48% |
| 10th | 93% | 72% | 94% | 36% |

As clear from Table 3, when the ion exchange treatment was practiced, the percent of impurities removed was stable and no reduction was observed even when chromatography was repeatedly conducted. On the contrary, in the case where the ion exchange treatment had not been conducted, the separability decreased with the repetition of chromatography and the percent of impurities removed was remarkably reduced, and thus it can be understood that by the ion exchange treatment, high separability can be maintained stably.

What is claimed is:

1. A process for the production of L-glutamic acid by fermentation, which comprises growing an L-glutamic-acid-producing microorganism in a fermentation medium containing as a carbon source a treated molasses product produced by a process which comprises a step (1) of adding an invertase or a mineral acid to cane molasses and keeping said cane molasses to which the invertase or the mineral acid has been added at a temperature and a pH suitable for inversion for a time required for almost all the amount of the sugar contained in said cane molasses to be inverted, a step (2) of passing said cane molasses treated with the invertase or the mineral acid after the step (1) through a column packed with a cation form cation exchange resin and subsequently passaging water having a pH in the range of 5–8 in an amount enough to elute 97% or more of the invert sugar through said resin column, and a step (3) of obtaining an eluate fraction containing the invert sugar after the step (2) as the carbon source.

2. The process of claim 1, wherein the process of producing the carbon source further comprises a step (4) of passing said cane molasses which has been treated with the invertase or the mineral acid through a column packed with a potassium ion form cation exchange resin after the step (1) and before the step (2) and where the cation form cation exchange resin in the step (2) is a posassium ion form cation exchange resin.

3. The process of claim 1 wherein the mineral acid is hydrochloric acid or sulfuric acid.

4. The process of claim 1 where the molasses is waste molasses.

5. the process of claim 1 wherein an invertase is added and the invertase is obtained from yeast microbial cells having invertase activity selected from the group consisiting of the genuses Saccharomyces, Candida, Mycotorula, Debarymyces, Pichia, Hansenula, and Torulopsis; and further, wherein said yeast microbial cells are obtained by culturing said yeast cells in a medium comprising molasses, glucose, pulp-production waste liquor, soybean whey, food industry waste liquor, or juice.

6. The process of claim 1 wherein, prior to step 2, the molasses resulting from step 1 is subjected to ultra-high speed centrifugation to remove solids contained in the molasses resulting from step 1.

7. The process of claim 6 wherein step 1 is carried out between 20° and 60° C.

8. The process of claim 7 wherein step 1 is carried out for between 5 and 20 hours.

9. The process of claim 8 wherein the concentration of the invert sugar to be passed through the column is in the range 35 to 45 g/dl.

10. The process of claim 1 wherein step 1 is conducted by adding invertase to a solution of molasses which is in a concentration of between 10 and 50 g/dl.

11. The process of claim 1 wherein the cation exchange resin is in the sodium or potassium form and is contained in a column equipped with a heat retaining jacket wherein the resin is maintained at a temperature of from 50° to 90° C., wherein the concentration of invert sugar which is passed through the column is in the range 15 to 50 g/dl and further, wherein a liquid passage rate through the column is in the range of between 0.5 and 2 S.V.

* * * * *

UNITED STATES PATENT AND TRADEMARK OFFICE
CERTIFICATE OF CORRECTION

PATENT NO. : 4,543,330

DATED : September 24, 1985

INVENTOR(S) : Morimoto Hideyuki, et al

It is certified that error appears in the above-identified patent and that said Letters Patent is hereby corrected as shown below:

Title page:

-- The priority information on the Letters Patent is incorrect. Please omitt these priority numbers:

Nov. 10, 1982    Japan    57-197139

Nov. 10, 1982    Japan    57-197138--

Signed and Sealed this

Fourteenth Day of January 1986

[SEAL]

Attest:

DONALD J. QUIGG

Attesting Officer      Commissioner of Patents and Trademarks